United States Patent [19]

Halleck et al.

[11] 4,014,347
[45] Mar. 29, 1977

[54] TRANSCUTANEOUS NERVE STIMULATOR DEVICE AND METHOD

[75] Inventors: Michael E. Halleck, Boulder; Thomas H. Thomson, Longmont, both of Colo.

[73] Assignee: Staodynamics, Inc., Longmont, Colo.

[22] Filed: May 27, 1975

[21] Appl. No.: 581,292

[52] U.S. Cl. .................................. 128/422
[51] Int. Cl.² ............................... A61N 1/36
[58] Field of Search ............ 128/419 R, 421, 422, 128/423

[56] References Cited
UNITED STATES PATENTS

| | | | |
|---|---|---|---|
| 3,373,747 | 3/1968 | Tapper | 128/422 |
| 3,521,641 | 7/1970 | Farensbach | 128/422 |
| 3,791,373 | 2/1974 | Winkler et al. | 128/422 |
| 3,881,494 | 5/1975 | Paul, Jr. | 128/421 |
| 3,897,789 | 8/1975 | Blanchard | 128/422 |
| 3,902,502 | 9/1975 | Liss et al. | 128/422 |
| 3,911,930 | 10/1975 | Hagfors et al. | 128/421 |
| 3,946,745 | 3/1976 | Lai et al. | 128/421 |

*Primary Examiner*—Robert W. Michell
*Assistant Examiner*—Lee S. Cohen
*Attorney, Agent, or Firm*—O'Rourke, Harris & Hill

[57] ABSTRACT

A transcutaneous nerve stimulator as disclosed that is useful for suppression of organic pain. The stimulator device is relatively small in overall dimensions and is therefore portable yet provides a rectangular waveform with the output signal produced being sufficient to drive a capacitive resistance load of at least 2.2K ohms in parallel with 0.1Mfd with a maximum rise and fall time of 12 microseconds. The device is powered by a pair of NI-CD batteries providing a 2.5 volt input and produces a maximum 80 volt peak pulse output having a maximum duration of .10 milliseconds at a pulse rate between 20pps and 180pps. Potentiometers are provided to vary the pulse rate, the duty cycle, and output pulse amplitude as is necessary or desirable for a particular patient. The device includes an oscillator that controls the pulse rate of the output from a variable one-shot multivibrator with the output pulses from the multivibrator being coupled through a power amplifier to the primary winding of a step-up transformer, the secondary winding of which transformer is connected through a voltage clamp and variable I.E. mode circuit to the output leads from the device. The disclosed method includes generating a rectangular waveform and producing an output that is sufficient to drive a capacitive resistance load of at least 2.2K ohms in parallel with 0.1Mfd with a maximum rise and fall time of 12 microseconds.

20 Claims, 5 Drawing Figures

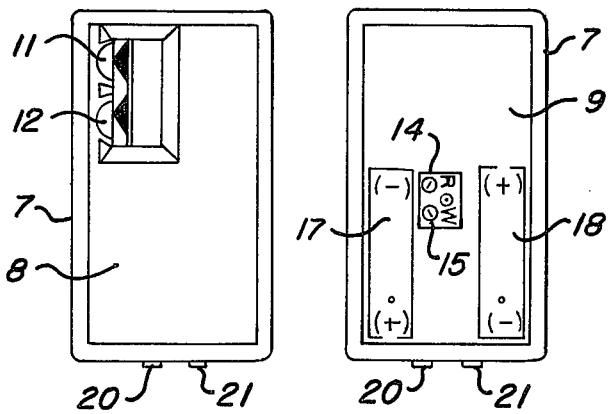
Fig_1  Fig_2
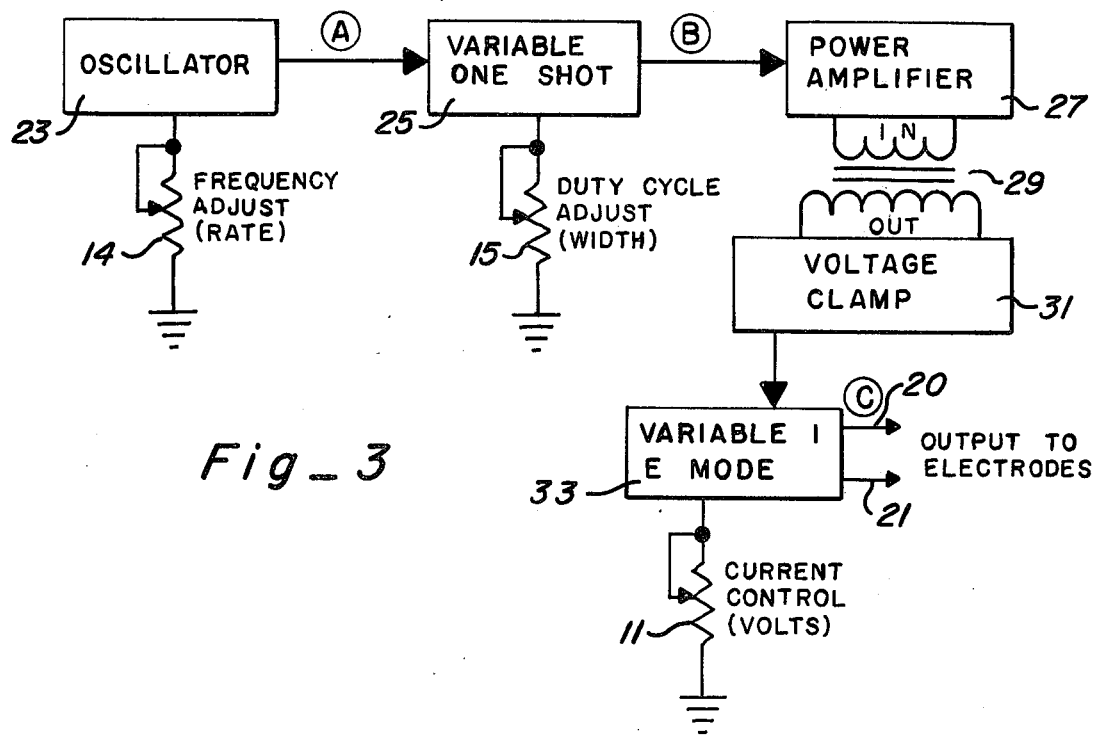
Fig_3
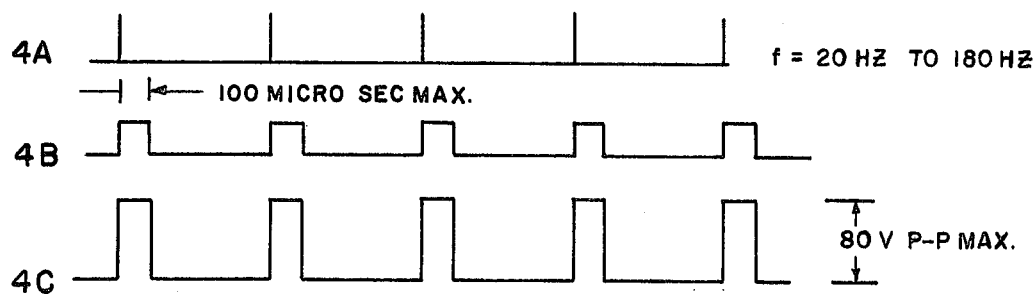
Fig_4

TRANSCUTANEOUS NERVE STIMULATOR DEVICE AND METHOD

FIELD OF THE INVENTION

This invention relates to transcutaneous nerve stimulation and more particularly relates to a transcutaneous nerve stimulating device and method for suppression of organic pain, without noxious sensation.

BACKGROUND OF THE INVENTION

Early attempts to suppress organic pain and other neurophysiological effects utilizing electrical signals occurred as early as about 2000 years ago when gout was apparently successfully treated by placing the extremities of a patient in a tub of water filled with Torpedo fish or electric eels. Later headaches were treated using a similar approach. A detailed, scientific investigation was then later conducted by Professor Galvani, professor of anatomy at the University of Bologna, and this is believed to have led to the development, during the 19th century, of electrical equipment for suppression of organic pain.

Among early patent literature, U.S. Pat. Nos. 646,793 (Bentz, issued in 1900), 872,148 (Raymond and Vetter, issued in 1907), 1,059,090 (Tibbals, issued in 1913), 1,305,725 (Kent, issued in 1919), 1,667,451 (Arnberg, issued in 1928), and 1,908,688 (Call, issued in 1933) are all directed to therapeutic devices wherein electricity was utilized as a stimulant.

During the 1950's, U.S. Pat. Nos. 2,622,601 (Nemec, issued in 1952), 2,624,342 (DiPerna, issued in 1953), and 2,771,554 (Gratzl, issued in 1956) were issued directed to electrotherapeutic devices in which the output signals included pulses with at least one of these devices including means to vary the magnitude, rate, and duration of the produced pulses.

With respect to more recently issued patents, U.S. Pat. No. 2,915,066 (Parodi, issued in 1959) is directed to an electro-stimulo-therapy apparatus that utilizes a step-up transformer, U.S. Pat. No. 3,645,267 (Hagfors, issued in 1972) is directed to a nerve stimulator that utilizes an output signal of increasing amplitude, U.S. Pat. No. 3,727,616 (Lenzkes, issued in 1973) is directed to an electronic stimulator that utilizes a CW signal of two frequencies and an implanted receiver, U.S. Pat. No. 3,794,022 (Nawracaj et al, issued in 1974) is directed to an electrotherapeutic device having dual oscillators to apply square wave pulses of increasing duration, U.S. Pat. No. 3,817,252 (Maurer, issued in 1974) is directed to a specific electrode for use in transcutaneous nerve stimulation, U.S. Pat. No. 3,817,254 (Maurer, issued in 1974) is directed to a transcutaneous stimulator in which a series of pulses are produced with each pulse having frequency components substantially ninety percent of the energy of which is specified to fall within substantially 100Hz, to 5,000Hz, and U.S. Pat. No. 3,835,833 (Limoge, issued in 1974) is directed to a method for obtaining neurophysiological effects and utilizes a composite signal.

It has been suggested that electrical impulses arriving at the central nervous system through large myelinated afferant nerve fibers exerted a modulating influence over impulses arriving later via slower-paced "A-delta and C fibers". Later, a so-called "Gate Control Hypothesis" was developed and this hypothesis is that pain relief following peripheral nerve stimulation is due to the inhibition of the small myelinated or unmyelinated fibers by electrically activating the large myelinated fibers. Still later, demonstrated relief of trigeminal neuralgia with implanted electrodes in the region of the trigeminal ganglion was shown.

Work in electrically stimulating sensory fibers of the spinal cord to suppress pain has resulted in the clinical use of implanted dorsal column stimulators (DCS). Following this, in 1967, Dr. Sweet at the Massachusetts General Hospital developed a transcutaneous nerve stimulator (TNS) as a means for screening DCS implant candidates. The TNS proved effective as a noninvasive, non-destructive modality for suppressing pain, and it was therefore developed as an independent modality. Dr. Burton at Temple University and Dr. Long at the University of Minnesota have reported that the TNS technique holds great promise, if problems of size, weight, electrode contact, and the unpleasant noxious response at the electrodes, can be resolved.

As can be seen from the foregoing, electrical signals utilizing a multitude of various waveforms within a specified frequency spectrum have been suggested and/or used to excite peripheral nerves to reduce or eliminate pain transmission to the brain. In addition, many different techniques have been attempted for the purpose of eliminating, or at least decreasing, the concurrent noxious sensations produced by the stimulating waveforms.

The techniques suggested have ranged in complexity from simple adjustments of rate, frequency and voltage to elaborate and complicated electronic circuits. However, none of the prior art electrical stimulator techniques or equipment have successfully solved all of the problems in this area and, more particularly, have not solved the noxious sensation problem.

SUMMARY OF THE INVENTION

This invention provides an improved transcutaneous nerve stimulating device and method that is portable yet produces a pulse output signal capable of suppressing organic pain over long periods of time without causing the patient appreciable discomfort due to the presence of a noxious sensation.

It is therefore an object of this invention to provide an improved transcutaneous nerve stimulating device.

It is another object of this invention to provide an improved transcutaneous nerve stimulating device that is portable.

It is still another object of this invention to provide an improved transcutaneous nerve stimulating device that requires only a 2.5 volt D.C input to produce a maximum 80 volt pulse output.

It is yet another object of this invention to provide an improved transcutaneous nerve stimulating device that produces an output signal sufficient to drive a capacitive resistance load of at least 2.2K ohms parallel with 0.1Mfd with maximum rise and fall time of 12 microseconds.

It is still another object of this invention to provide an improved transcutaneous nerve stimulating device that includes an oscillator, a one-shot multivibrator, a step-up transformer, a clamp circuit and/or redundent parallel clamp circuit, and an I.E. mode circuit.

It is still another object of this invention to provide an improved transcutaneous nerve stimulating method.

It is yet another object of this invention to provide an improved pain suppression method that provides a signal sufficient to drive a capacitive resistance load of at least 2.2K ohms paralleled with 0.1Mfd with a maximum rise and fall time of 12 microseconds.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the patent application for the principles thereof, and in which:

FIG. 1 is a front view of the transcutaneous nerve stimulating device of this invention;

FIG. 2 is a rear view of the transcutaneous nerve stimulating device of this invention as shown in FIG. 1;

FIG. 3 is a block diagram of the transcutaneous nerve stimulator of this invention;

FIG. 4 is a series of waveforms relating to the block diagram of FIG. 3; and

DESCRIPTION OF THE INVENTION

Figure 5:
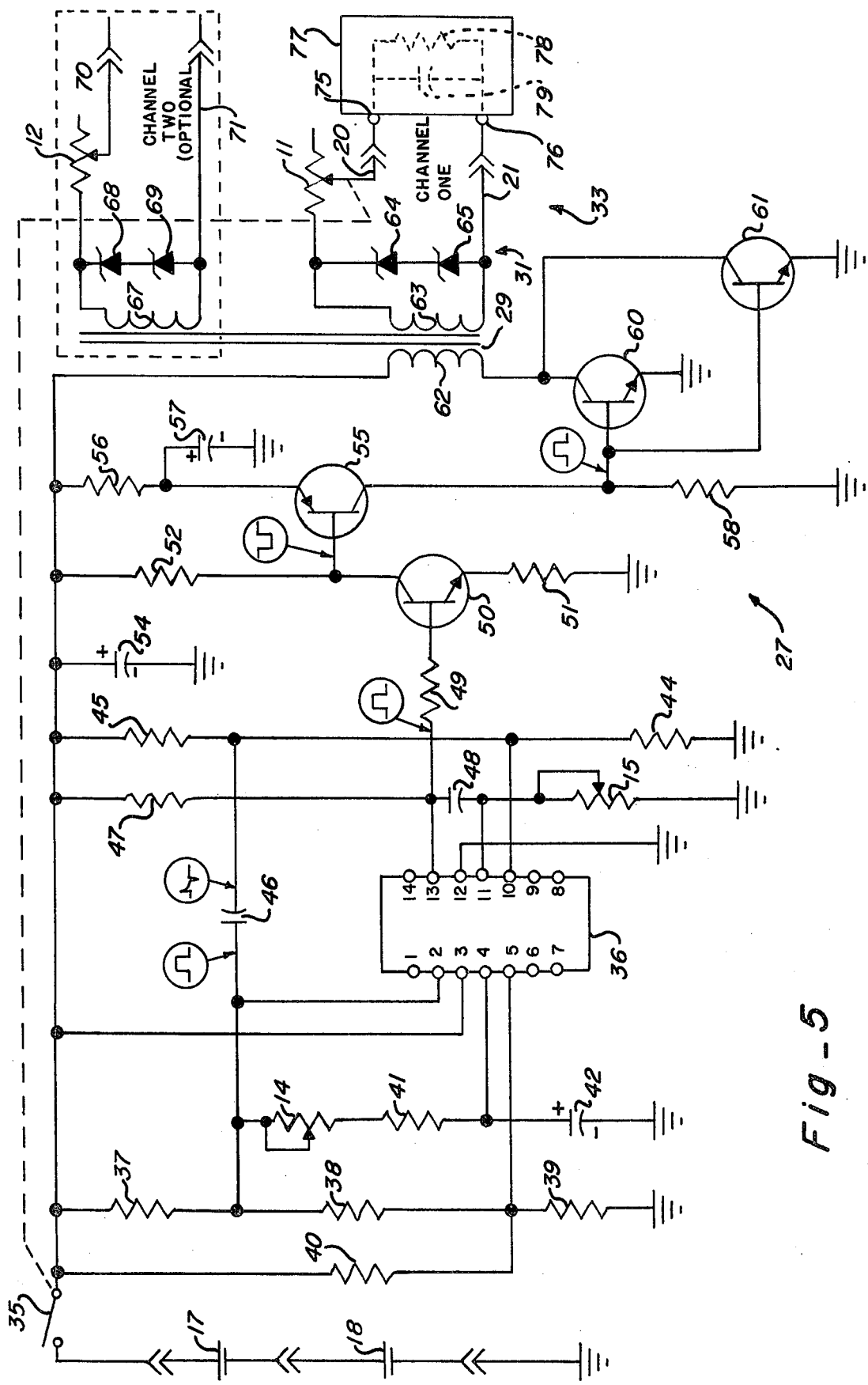
FIG. 5 is a combined block and schematic diagram of the transcutaneous nerve stimulating device of this invention as shown in block form in FIG. 3.

The transcutaneous nerve stimulating device of this invention is a portable, battery operated device no larger than about the size of a 100mm pack of cigarettes. The device is capable of generating an electrical signal of the proper voltage, pulse rate and duty cycle for reducing or eliminating pain in human patients. The electrical signal is commonly applied to the patient through electrodes connected between the patient and the device with the electrodes being in contact with the skin and normally being positioned over the nerve that carries the pain message to the brain. The electrical signal thus supplied is conducted through the skin and into the nerve fiber and will either "gate off" the pain carrying message to the brain or supply sufficient interference to the pain signal to either reduce or eliminate its transmission to the brain. In this invention, the electrical signal supplied is such that the prior art problems are diminished, or entirely eliminated, including the problem of a patient experiencing a noxious sensation.

The approach used to solve this problem relates directly to prior experimental data generated within and in connection with the human body, but this prior experimental data now utilized was then unrelated to transcutaneous nerve stimulation when obtained.

In 1956, Dalziel performed experiments on over 100 subjects to perceive current flowing into the body through electrodes. The threshold of sensation was 5.2MA for direct current and 1.1MA for 60Hz alternating current. Dalziel further found that the threshold of sensation for women was two-thirds that of men.

Dalziel conducted another experiment measuring the threshold for sensation for different frequencies of sinusoidal current. For 99½% of the subjects tested, he found the following results:

1. Above about 300Hz, the threshold of perception rises as frequency is increased (1.6MA);

2. At about 8,000Hz, the threshold is 10 times as great as at 300Hz (16MA); and

3. At about 70K Hz, the threshold is 100 times as great as at 300Hz (160MA).

In 1962, Geddes confirmed the results of Dalziel. Based on the studies of Dalziel, Geddes and other internal studies, and relating this information directly to the problems of transcutaneous nerve stimulation, we have discovered that frequencies in the high K HZ range or DC voltages, or both, in combination must be employed if noxious sensations of the applied waveform are to be avoided. This indicates that the waveform must be a rectangular pulse having a fast rise and fall time, with essentially 0% droop with the waveform thus generally following the strength-duration characteristics of the human body as observed by the studies set forth hereinabove.

However, we have also discovered that the body impedance for the pulse described can be approximated by a parallel connected resistance and capacitance combination of 2.2K ohms and 0.1Mfd at the electrode site and for contemplated pulse shapes to be utilized.

It is therefore evident that the waveform described must have sufficient power to drive the 0.1Mfd component of the body impedance to acquire fast rise and fall time at the leading and trailing edge of the rectangular pulse.

If this waveform is coupled to the peripheral nerve carrying the pain message, the pain message will not arrive at the brain, provided that this waveform holds the nerve in the absolute refractory period state blocking the pain pulse signal. Furthermore, the concurrent noxious sensations generally produced by the waveform will be eliminated since the fast rise and fall time of the leading and trailing edges are high frequency components to which the human body nociceptors cannot respond.

Nerves transmit electrical signals which are generated by a chemical reaction, as follows:

Nerves consist of lipid materials supported by a protein matrix. The membrane is a few hundred Angstroms thick and is porous to small molecules. The membrane is semipermeable with the pores large enough to allow positive ions to flow through while the negtive ions are blocked. Kinetic motion causes constant ionic movement and when an excess of positive ions is present on one side, with an excess of negative ions on the other, a potential difference will result between the two sides, provided the ion concentration is greater on one side than the other. EMF (Millivolts) = 61 log concentration 1/CONCENTRATION 2 If concentration rate = 10 to 1 EMP = 61 log 10 = 61 millivolts.

The active transport mechanism of the cell membrane transports Na from the inside of the cell to the outside and K from the outside to the inside, causes a resting potential gradient of approximately 85 millivolts. The membrane is 20 to 100 times as permeable to K as to Na.

It is the positive ions which create the resting potential gradient and effect the negative or chlorine ions to concentrate at the outside of the cell with only a few remaining inside the cell.

When the membrane becomes excited by an electro chemical pulse or other means, and is stimulated, the membrane momentarily becomes more permeable to Na than to K. The rapid change in permeability of the membrane to Na and K causes the electro chemical impulse to be transmitted along the nerve fiber.

In resting state, K passes with ease through the membrane while Na is impeded. K concentration inside the cell is very high compared to outside and therefore positive charges diffuse to the outside of the cell with negative charges to the inside.

Potassium — K — Atomic No. 19 Atomic weight 39.100 — valence + 1

Sodium — Na — Atomic No. 11 Atomic weight 22.991 — valence + 1

Chlorine — Cl — Atomic No. 17 Atomic weight 35.457 — valence − 1

Carbon — C — Atomic No. 6 Atomic weight 12.011 — valence

Since the resting permeability of the membrane to Na is very small, compared to K, then the resting potential will approach that which would develop if only K were defusable through the membrane.

$$EMF = 61 \log \frac{K1}{Ko}$$ $K1 = K$ concentration inside nerve
$Ko = K$ concentration outside nerve Should an action potential (break surface of membrane, crush membrane, chemical action, electrical stimuli) be applied to a resting membrane, the resting potential gradient decreases to zero or goes to a negative voltage for about 0.5 milliseconds in large fibers and then returns to its normal resting potential. The action potential causes electrical waves to flow along the inner and outer surfaces of the nerve and excites the fibers further down the line initiating another action potential, etc., causing propagation of the electro chemical impulse along the nerve to the brain.

It is known that once an action potential is initiated, the pain signal travels to the end of the nerve at a speed of 0.5 to 15 meters per second, and varies as the square root of the cross sectional diameter of the nerve. The magnitude of the pain signal is constant, regardless of the intensity of stimulation. For example, if a human member, such as a finger for example, becomes subject to heat (from a cigarette or a blow torch, for example) the transmitted pain waveform will be about 130 millivolts. The intensity with which the pain is felt is determined by the frequency of these constant amplitude pain waveforms and the number of nerve fibers carrying these constant amplified waveforms. After the nerve fires, there is an "absolute Refractory Period" at which time the nerve will not fire again regardless of the stimulus strength and to stimulate the nerve a second time after it has been triggered requires a much stronger stimulus than normally used. Also, if the nerve has been excited to carry a train of pulses, its recovery to the normal "resting potential" of about +85 millivolts is slower than after a single impulse.

If a large number of pulses or a train of pulses excites a nerve, fatigue of the nerve can occur which will then require a larger external stimulus for re-triggering.

With the above information in mind, it becomes evident that not only is power required to provide fast rise and fall times for the rectangular waveform to trigger the nerve and not induce noxious side effects, but the magnitude of this waveform must be of sufficient amplitude to first break down the skin resistance and create a lower impedance from the electrodes to the nerve proper and second, supply appropriate current to the nerve during the absolute refractory period to not allow the pain message waveform to reoccur. In other words, a constant voltage waveform is first required, and then a constant current. We have discovered that a compromise between constant voltage and constant current adjusted to the needs of the individual patient works well with approximately 85% of the patients tested.

Obviously, there are many variations in the method of designing circuitry to fulfill this requirement ranging from a simple resistor to elaborate electronic circuitry, and an example of a working embodiment of this invention is set forth hereinafter.

Referring now to the drawings, the numeral 7 indicates generally the transcutaneous nerve stimulating device of this invention. As shown in FIGS. 1 and 2, the device is packaged so as to be small and portable and has a front side 8 and a rear side 9 with controls on each side. At the front side, there is located a pair of finger actuatable controls 11 and 12 which control the peak pulse voltage output signal for the device (and are indicated as potentiometers in FIG. 5).

At the rear side of the device, a pair of screw driven actuatable controls 14 and 15 are provided which control the pulse rate and pulse width of the rectangular wave pulses generated by the device (and are also indicated as potentiometers in FIG. 5).

While contained within the case, or package, FIG. 2 depicts placement of batteries 17 and 18, the batteries being preferably NI-CD batteries providing 1.25 volts each so that when connected in series 2.5 volts is supplied to the device as the sole power supply. FIGS. 1 and 2 also show a pair of outputs 20 and 21 from which the output signals are coupled to electrodes in contact with the skin of the patient.

Referring now to the block diagram of FIG. 3, a free running oscillator 23 has potentiometer 14 connected therewith so that the frequency of the output signal from the oscillator can be varied between 20 and 180 pulses per second with a typical output being shown in FIG. 4. Each pulse has frequency components from 5K Hz to 1meg Hz with at least 90% of the energy being within this range.

The output signals from oscillator 23 are used to control pulses produced at variable one-shot multivibrator 25 which has connected therewith potentiometer 15 for adjustment of the duty cycle (pulse width) of the rectangular pulses produced at the output of the multivibrator. As shown in FIG. 4b, multivibrator 25 produces a rectangular output pulse for each control pulse received from oscillator 23. As also indicated in FIG. 4b, the pulse width is variable between 0 and 100 microseconds maximum.

Rectangular pulses generated by multivibrator 25 are coupled through power amplifier 27 to the primary winding of step-up transformer 29, the secondary winding of which transformer is connected with voltage clamp 31. Power amplifier 27 supplies sufficient gain to drive the step-up transformer to an output voltage greater than the clamp volatage (loaded or no load), and the voltage clamp 31 limits the voltage swing to approximately 80 volts or less, peak to peak, and therefore supplies a fast rise and fall time rectangular pulse to variable I.E. mode circuit 33.

Variable I.E. mode circuit 33 provides a constant voltage, a constant current, or any adjustable or fixed condition between these two modes to a predetermined load.

It has been found that a human patient (the normal predetermined load) has an impedance equivalent to approximately 2.2K ohms paralleled by 0.1Mfd at the electrical conditions described, as brought out hereinabove. The variable I.E. mode circuit, because of its location, thus forms a voltage divider with the patient and provides less inhibition to fast rise and fall time of the rectangular pulse to the patient as well as appropriate current and voltage to compensate for a changing electrical load presented by the patient.

When the foregoing two conditions are met, a proper waveform is provided by the device to the patient through the electrodes to successfully block out pain messages and is accommodated to by sensory means, thus eliminating or at least reducing electrical sensation at the electrodes.

Referring now to FIG. 5, batteries 17 and 18 are shown connected in series to provide power to the device through switch 35 when the switch is closed. As shown, power is provided to integrated circuit 36 (which includes oscillator 23 and multivibrator 25) with pin 2 of the integrated circuit being connected to the power supply line through resistor 37, which resistor is part of a voltage divider that includes resistors 38 and 39 in series therewith. A resistor 40 is in parallel with resistors 37 and 38 with the junction of resistors 38 and 39 being connected to pin 5 of integrated circuit 36. Pin 4 of integrated circuit 36 is connected to the junction of resistors 37 and 38 through potentiometer 14 and resistor 41 connected in series with one another. In addition, the junction of pin 4 and resistor 41 has a by-pass capacitor 42 to ground.

Resistors 44 and 45 are connected in series as a voltage divider between the power supply line and ground with the junction of resistors 44 and 45 being connected to pin 10 of integrated circuit 36 and to one side of capacitor 46, the other side to which capacitor is connected to pin 2 of the integrated circuit. Pin 13 of the integrated circuit is connected to the power supply line through resistor 47 and the junction of pin 13 and resistor 47 is connected to one side of capacitor 48, the other side of which capacitor is connected to pin 11 of the integrated circuit, and which pin is also connected through potentiometer 15 with ground.

The output from integrated circuit 36 (i.e., from multivibrator 25) is coupled from pin 13 through resistor 49 to the base of transistor 50. Transistor 50 has its emitter connected with ground through resistor 51 and its collector connected to the power supply line through resistor 52. In addition, the power supply line has a bypass capacitor 54 to ground.

The output from transistor 50 is coupled from the collector to the base of transistor 55. Transistor 55 has its emitter connected to the power supply line through resistor 56, with the junction of the emitter and resistor 56 having a capacitor 57 to ground connected therewith. The collector of transistor 55 is connected with ground through resistor 58 and directly connected to the bases of paralleled connected transistors 60 and 61.

The collectors of transistors 60 and 61 are connected to primary winding 62 and step-up transformer 29. As shown in FIG. 5, secondary winding 63 of step-up transformer 29 is connected with voltage clamp 31 which includes a pair of series connected Zener diodes 64 and 65, with the diodes being connected in parallel with secondary winding 63. If desired, a second pair of Zener diodes (not shown) can be utilized in parallel with diodes 64 and 65 for added protection against RF burns.

As also shown in FIG. 5, a second channel can be provided identical to the first channel if two outputs are desired for pain suppression at different locations on a patient. When the second, or optional, channel is utilized, a second secondary winding 67 of step-up transformer 29 is provided. Secondary winding 67 has a pair or series connected Zener diodes 68 and 69 connected in parallel with winding 67.

The output signal from the device is coupled through outputs 20 and 21 for channel 1 and 70 and 71 for the optional channel (channel 2). As indicated for channel 1, the predetermined load (i.e., a patient) has an equivalent impedance of approximately 2.2K ohms parallel with 0.01Mfd. This is indicated in FIG. 5 by lines 20 and 21 being connected to conventional electrodes 75 and 76 at a load 77 (i.e., a patient) presenting an equivalent impedance indicated by resistor 78 and capacitor 79 connected in parallel with one another as shown in FIG. 5.

In a working embodiment of this invention, the following components were utilized, it being realized that the listed components are for illustration only and the invention is not meant to be limited thereto:

Resistors: 14 - 0 to 10K; 15 - 0 to 10K; 37 - 4.7K; 38 - 47K; 39 - 3.3K; 40 - 47K; 41 - 2.2K; 44 - 100K; 45 - 470K; 47 - 4.7K; 49 - 1K; 51 - 10; 52 - 1K; 56 - 100; and 58 - 330.

Capacitors: 42 - 4.7Mfd; 46 - 120Pfd; 48 - 0.015Mfd; 54 - 400Mfd (800Mfd if channel 2 is included); and 57 - 10Mfd.

Transistors: 50 - 2N3904; 55 - 2N3905; and 60 and 61 - MJE3055.

Zener Diodes: 64, 65, 68, and 69 - 40 volt.

Integrated Circuit: 36 - MC3302P.

In operation, the patient (in conjunction initially with the doctor or his staff) places the two electrodes (or four if two channels are utilized) in contact with the skin in proximity to the spinal cord, nerve route, or peripheral nerve involved as may be necessary for the particular patient or pain involved. The patient or his doctor sets the pulse rate, pulse width, and voltage amplitude (initially the rate is normally set high and the amplitude and pulse width are set to one-half to two-thirds of maximum setting). Since settings vary from patient to patient, the settings are then adjusted (as may be the electrode placements also) so that radiations may or may not still be felt with ultimate adjustment of the controls being made until a minimum setting for each of the controls barely produces radiation. The electrode sensation will vanish but the radiation may or may not be felt. The device is then ready for prolonged periods of use in suppressing organic pain and further adjustment should not be needed (except possibly for minor adjustments) for use over long periods of time except that as the batteries discharge, the voltage will need to be adjusted to the appropriate level to occasionally compensate for this and the batteries will, of course, need periodic exchange). If rechargeable batteries are utilized, one set can be charged while another set is in use, and a third set for standby purposes can also be utilized.

While not meant to be limited thereto, the transcutaneous nerve stimulator of this invention has been successfully used to manage pain in a large number of chronic and acute pain cases, such as occurring from neuralgia (including herpes zoster, trigeminal neuralgia, trauma and multiple trauma of the spinal column, migraine and tension headaches), progressive conditions (such as arthritis and bursitus and cancer) and other assorted pains (such as post-surgical pain, labor pain and back strain pain).

In view of the foregoing, it is apparent that the improved transcutaneous nerve stimulator of this invention provides an improved device and method for suppression of organic pain.

What is claimed is:

1. A transcutaneous nerve stimulator for suppression of organic pain in a body, said stimulator comprising:
    pulse generator means for producing a rectangular waveform at a predetermined frequency, said pulse generator means including means for adjustment of said produced rectangular waveform; and
    output means connected with said pulse generator means to receive said rectangular waveform therefrom, said output means including a variable current-voltage mode circuit providing an AC output signal substantially without DC components and having a waveform with a fast rise and fall time no greater than about 12 microseconds with said waveform being sufficient to drive the impedance of a body positioned contiguous to said output means so as to be affected by said output signal whereby organic pain is suppressed in said affected body without causing noxious sensations despite receipt of said output signals by said affected body over an extended period of time.

2. The transcutaneous nerve stimulator of claim 1 wherein said stimulator includes a battery source of 2.5 volts connected with said pulse generator means and output means to drive the same.

3. The transcutaneous nerve stimulator of claim 2 wherein said battery source includes a pair of NI-CD batteries.

4. The transcutaneous nerve stimulator of claim 1 wherein said pulse generator means includes an oscillator and a one-shot multivibrator.

5. The transcutaneous nerve stimulator of claim 4 wherein said oscillator includes means for varying the frequency thereof.

6. The transcutaneous nerve stimulator of claim 1 wherein said output means includes a step-up transformer and pulse shaping means.

7. The transcutaneous nerve stimulator of claim 1 wherein said variable current-voltage mode circuit includes a variable resistor that cooperates with the impedance of said affected body to establish a variable current-voltage mode of operation.

8. The transcutaneous nerve stimulator of claim 1 wherein said variable current-voltage mode circuit of said output means includes means causing said output means to provide an output the frequency spectrum of which follows a strength-duration relationship sufficient to suppress pain without causing noxious sensations.

9. The transcutaneous nerve stimulator of claim 1 wherein said variable current-voltage mode circuit of said output means includes means causing said output to have a magnitude of sufficient amplitude to first break down the skin resistance of said affected body and create a lower impedance and then to supply appropriate current to suppress pain thereafter.

10. The transcutaneous nerve stimulator of claim 1 wherein said pulse generator means includes means to produce rectangular pulses each pulse of which has frequency components at least 90% of the energy of which is contained within a frequency range of 5K Hz to 1 meg Hz.

11. The transcutaneous nerve stimulator of claim 1 wherein said stimulator is compact and of sufficiently small size to be worn by a person.

12. A transcutaneous nerve stimulator for suppression of organic pain in a body, said stimulator comprising:
    an oscillator producing an output signal at a frequency of between about 20 and 180 Hz;
    a one-shot multivibrator connected with said oscillator and receiving the output signal therefrom, said one-shot multivibrator producing a rectangular output signal at the frequency of said output signal from said oscillator, said rectangular output signal having a pulse width no greater than about 100 $\mu$seconds;
    a step-up transformer having a primary winding receiving said output from said one-shot multivibrator and a secondary winding; and
    output means connected with said secondary winding of said transformer and providing an AC output signal substantially without DC components and having a waveform with a fast rise and fall time no greater than about 12 microseconds with said waveform being sufficient to drive the impedance of a body positioned contiguous to said output means so as to be affected by said output signal whereby organic pain is suppressed in said affected body without causing noxious sensations despite receipt of said output signals by said affected body over an extended period of time.

13. The transcutaneous nerve stimulator of claim 12 wherein said stimulator includes means for varying the pulse rate of said oscillator and the pulse width of said multivibrator.

14. The transcutaneous nerve stimulator of claim 12 wherein said output means includes a pulse forming circuit and I.E. mode circuit means.

15. The transcutaneous nerve stimulator of claim 12 wherein said oscillator and one-shot multivibrator are a part of an integrated circuit.

16. A transcutaneous nerve stimulator for suppression of organic pain in a human body, said stimulator comprising:
    an oscillator producing an output signal variable between about 20 and 180 pulses per second;
    frequency control means connected with said oscillator to control the frequency produced by said oscillator; p1 a one-shot multivibrator connected with said oscillator and producing rectangular wave output signals at a frequency determined by the output signal from said oscillator;
    width control means connected with said multivibrator to control the width of pulses produced by said multivibrator with said rectangular waveform produced by said one-shot multivibrator being no greater than about 100 $\mu$seconds;
    power amplifier means connected with said multivibrator and providing a rectangular pulse output signal in response to rectangular pulse signals received from said multivibrator;
    a step-up transformer having a primary winding connected to receive the output from said power amplifier means and a secondary winding;
    a pulse shaping means connected to said secondary winding of said transformer;

a variable I.E. mode circuit means connected to receive the output from said secondary winding of said transformer through said pulse shaping means and providing an AC output signal substantially without DC components and having a waveform with a fast rise and fall time no greater than about 12 microseconds; and electrode means connected to said I.E. mode circuit means to receive said AC output signal therefrom and adapted to be contiguous to a human body to suppress pain therein, said variable I.E. mode circuit means causing the output to said electrode means to drive the impedance of a human body contiguous to said electrode means and thereby suppress pain without causing noxious sensations despite application of said output to said human body over an extended period of time.

17. The transcutaneous nerve stimulator of claim 16 wherein said variable I.E. mode circuit means is a variable resistor connected with said electrode means so as to be in series with a human body contiguous to said electrode means.

18. A method for suppression of organic pain, said method comprising:

generating a rectangular AC waveform substantially without DC components sufficient to drive a capacitive resistance load having an impedance substantially equal to that of a patient and having a fast rise and fall time no greater than about 12 $\mu$seconds; and applying said generated waveform to a human patient for an extended period of time to suppress organic pain in said patient without causing noxious sensations in said patient.

19. The method of claim 18 wherein said applied waveform has a magnitude sufficient to first break down the skin resistance of said human patient and create a lower impedance and then to supply appropriate current to suppress pain thereafter.

20. The method of claim 18 wherein each of said rectangular waveforms generated has foregoing components at least 90% of the energy of which is contained within a foregoing range of 5K Hz to 1meg Hz.

* * * * *